(12) United States Patent
Bullock

(10) Patent No.: US 7,528,614 B2
(45) Date of Patent: May 5, 2009

(54) APPARATUS AND METHOD FOR VOLTAGE CONTRAST ANALYSIS OF A WAFER USING A TILTED PRE-CHARGING BEAM

(75) Inventor: Eugene Thomas Bullock, Fremont, CA (US)

(73) Assignee: Applied Materials, Inc., Santa Clara, CA (US)

( * ) Notice: Subject to any disclaimer, the term of this patent is extended or adjusted under 35 U.S.C. 154(b) by 243 days.

(21) Appl. No.: 11/020,639

(22) Filed: Dec. 22, 2004

(65) Prior Publication Data

US 2006/0134810 A1 Jun. 22, 2006

(51) Int. Cl.
G01R 31/302 (2006.01)

(52) U.S. Cl. .................................................. 324/752

(58) Field of Classification Search ................. None
See application file for complete search history.

(56) References Cited

U.S. PATENT DOCUMENTS 3,638,015 A 1/1972 Browning et al.

(Continued)

FOREIGN PATENT DOCUMENTS

CN 1333466 1/2002

(Continued)

OTHER PUBLICATIONS

Variably Shaped Electron Beam Lithography System, EB55:II Electron Optics, N. Saitou et al., J. Vac. Sci Technol., 19(4), Nov./Dec. 1981, pp. 1087-1093.

(Continued)

*Primary Examiner*—Jermele M Hollington
(74) *Attorney, Agent, or Firm*—Tarek N. Fahmi

(57) ABSTRACT

A method for electrically testing a wafer that includes: receiving a wafer having a first layer that is at least partly conductive and a second layer formed over the first layer, following production of openings in the second layer; directing towards the wafer a first set of beams of charged particles that are oriented at a first set of angles in relation to the wafer, wherein each angle of the first set of angles deviates substantially from normal, so as to pre-charge an area of the second layer without substantially pre-charging the first layer; scanning the area of the wafer by a second set of beams of charged particles that are oriented at a second set of angles in relation to the wafer, and collecting charged particles scattered from the area wafer. A system for electrically testing a semiconductor wafer, the system including: at least one charged particle beam source; at least one detector, adapted to collect charged particles scattered from the wafer; wherein the wafer comprises a first layer that is at least partly conductive and a second layer formed over the first layer, following production of openings in the second layer; wherein the system is adapted to: (i) direct towards the wafer a first set of beams of charged particles that are oriented at a first set of angles in relation to the wafer, wherein the first angle deviates substantially from normal, so as to pre-charge an area of the second layer without substantially pre-charging the first layer; (ii) scan the area of the wafer by a second set of beams of charged particles that are oriented at a second set of angles in relation to the wafer, and collect charged particles scattered from the area of the wafer.

21 Claims, 4 Drawing Sheets

U.S. PATENT DOCUMENTS

| | | | |
|---|---|---|---|
| 3,701,979 | A | 10/1972 | Smith et al. |
| 3,930,181 | A | 12/1975 | Pfeiffer |
| 4,068,218 | A | 1/1978 | Likuski |
| 4,221,965 | A | 9/1980 | Konishi et al. |
| 4,342,949 | A | 8/1982 | Harte et al. |
| 4,376,249 | A | 3/1983 | Pfeiffer et al. |
| 4,415,851 | A | 11/1983 | Langner et al. |
| 4,417,203 | A | 11/1983 | Pfeiffer et al. |
| 4,443,278 | A | 4/1984 | Zingher |
| 4,567,402 | A | 1/1986 | Mourier |
| 4,575,630 | A | 3/1986 | Lukianoff |
| 4,607,167 | A * | 8/1986 | Petric .................... 250/492.2 |
| 4,712,057 | A | 12/1987 | Pau |
| 4,725,730 | A | 2/1988 | Kato et al. |
| 4,785,176 | A | 11/1988 | Frosien et al. |
| 4,825,087 | A | 4/1989 | Renau et al. |
| 4,843,330 | A | 6/1989 | Golladay et al. |
| 4,855,673 | A | 8/1989 | Todokoro |
| 4,896,045 | A | 1/1990 | Okunuki et al. |
| 4,912,052 | A | 3/1990 | Miyoshi et al. |
| 4,926,054 | A | 5/1990 | Frosien |
| 4,939,360 | A | 7/1990 | Sakai |
| 4,943,769 | A | 7/1990 | Golladay et al. |
| 4,972,083 | A | 11/1990 | Taya et al. |
| 4,983,832 | A | 1/1991 | Sato |
| 5,030,908 | A | 7/1991 | Miyoshi et al. |
| 5,057,773 | A | 10/1991 | Golladay et al. |
| 5,089,710 | A | 2/1992 | Kikuchi et al. |
| 5,136,540 | A | 8/1992 | Hayashi et al. |
| 5,148,034 | A | 9/1992 | Koike |
| 5,187,371 | A | 2/1993 | Matsui et al. |
| 5,214,289 | A | 5/1993 | Betsui |
| 5,254,856 | A | 10/1993 | Matsui et al. |
| 5,304,801 | A | 4/1994 | Arai |
| 5,401,972 | A | 3/1995 | Talbot |
| 5,412,209 | A | 5/1995 | Otaka et al. |
| 5,420,433 | A | 5/1995 | Oae et al. |
| 5,442,183 | A | 8/1995 | Matsui et al. |
| 5,493,116 | A | 2/1996 | Toro-Lira et al. |
| 5,502,306 | A | 3/1996 | Meisburger et al. |
| 5,528,048 | A | 6/1996 | Oae et al. |
| 5,578,821 | A | 11/1996 | Meisberger et al. |
| 5,602,489 | A | 2/1997 | El-Kareh et al. |
| 5,614,725 | A | 3/1997 | Oae et al. |
| 5,644,132 | A | 7/1997 | Litman et al. |
| 5,659,172 | A | 8/1997 | Wagner et al. |
| 5,757,198 | A | 5/1998 | Shida et al. |
| 5,777,327 | A | 7/1998 | Mizuno |
| 5,872,358 | A | 2/1999 | Todokoro et al. |
| 5,905,266 | A | 5/1999 | Larduinat et al. |
| 5,976,328 | A * | 11/1999 | Azuma et al. ............. 250/492.3 |
| 5,986,263 | A | 11/1999 | Hiroi et al. |
| 6,072,178 | A | 6/2000 | Mizuno |
| 6,150,185 | A | 11/2000 | Hahm et al. |
| 6,172,363 | B1 | 1/2001 | Shinada et al. |
| 6,187,687 | B1 | 2/2001 | Plat et al. |
| 6,252,412 | B1 | 6/2001 | Talbot et al. |
| 6,433,561 | B1 | 8/2002 | Satya et al. |
| 6,509,750 | B1 * | 1/2003 | Talbot et al. ................ 324/750 |
| 6,586,736 | B1 | 7/2003 | McCord |
| 6,627,884 | B2 | 9/2003 | McCord et al. |
| 6,674,075 | B2 | 1/2004 | Petrov et al. |
| 6,975,125 | B2 * | 12/2005 | Yamada et al. .............. 324/751 |
| 2001/0223345 | | 9/2001 | Ishimoto |
| 2002/0093350 | A1 | 7/2002 | Yamada |
| 2002/0179855 | A1 * | 12/2002 | Muraki .................. 250/492.22 |
| 2003/0218133 | A1 | 11/2003 | Petrov et al. |
| 2004/0056207 | A1 | 3/2004 | Petrov et al. |
| 2004/0173746 | A1 | 9/2004 | Petrov et al. |
| 2006/0054816 | A1 * | 3/2006 | Bullock ...................... 324/751 |

FOREIGN PATENT DOCUMENTS

| | | |
|---|---|---|
| DD | 126382 | 7/1977 |
| DE | 4430456 | 9/1995 |
| EP | 0066070 | 12/1982 |
| EP | 0151720 | 8/1985 |
| EP | 0312083 | 4/1988 |
| EP | 0309956 | 4/1989 |
| EP | 0345772 A2 | 12/1989 |
| EP | 0781977 | 2/1997 |
| EP | 0853243 | 7/1998 |
| EP | 1045426 A2 | 10/2000 |
| GB | 2067348 A1 | 7/1981 |
| JP | 59079544 | 5/1984 |
| JP | 60136235 | 7/1985 |
| WO | 98/32153 | 7/1998 |
| WO | 99/34397 A1 | 7/1999 |
| WO | 01/45136 A1 | 6/2001 |

OTHER PUBLICATIONS

Testing Integrated Circuit Microstructures Using Charging-Induced Voltage Contrast, T.J. Aton et al., J. Vac. Sci Technol., B 8(6), Nov./Dec. 1990, pp. 2041-2044.

Analysis of Silicide Process Defects by Non-Contact Electron-Beam Charging, K.A. Jenkins et al., 30th annual proceedings reliability physics 1992, 3/31, 4/1. 4/2, 1992, pp. 304-308.

L. Reimer, Image Formation in Low-Voltage Scanning Electron Microscopy, 1993, pp. 74-75.

The electrostatic moving objective lens and optimized deflection systems for microcolumns, M.G.R. Thomson, J. Vac. Sci Technol., B 14(6), Nov./Dec. 1996, pp. 3802-3807.

Applied Materials Israel, Ltd., PCT/US2004/018159, International Search Report, Nov. 11, 2004, 5pp.

Patent Abstracts of Japan, 20000174077, Jun. 23, 2000, 1pg.

Patent Abstract of Japan, 2002083849, Mar. 22, 2002, 1pg.

An Inline Process Monitoring Method Using Electron Beam Induced Substrate Current, Yamada et al., 5pp, Microelectronics Reliability, Jul. 27, 2000.

* cited by examiner

```
┌─────────────────────────────────────────────────────────────┐
│   determining the first angle in response to an aspect ratio│
│               of at least one contact hole                   │
│                           305                                │
└─────────────────────────────────────────────────────────────┘
                              │
┌─────────────────────────────────────────────────────────────┐
│   receiving a wafer having a first layer that is at least   │
│  partly conductive and a second layer formed over the first │
│  layer, following production of openings in the second layer│
│                           310                                │
└─────────────────────────────────────────────────────────────┘
                              │
┌─────────────────────────────────────────────────────────────┐
│  directing towards the wafer a first set of beams of charged│
│ particles (said set may include one or more first beams) that│
│  are oriented at a first set of angles said set may include │
│   one or more first angles) in relation to the wafer, whereas│
│   the each of the first set of angles deviates substantially│
│  from normal, so as to pre-charge an area of the second layer│
│       without substantially pre-charging the first layer.   │
│                           320                                │
└─────────────────────────────────────────────────────────────┘
                              │
┌─────────────────────────────────────────────────────────────┐
│  scanning the area of the wafer by a second set of beams of │
│   charged particle beam that are oriented at a second set of│
│    angles in relation to the wafer, and collecting charged  │
│           particles scattered from the area wafer.          │
│                           330                                │
└─────────────────────────────────────────────────────────────┘
                              │
┌─────────────────────────────────────────────────────────────┐
│  generating an image of the area of the wafer in response to│
│             the collected charged particles.                │
│                           340                                │
└─────────────────────────────────────────────────────────────┘
```

APPARATUS AND METHOD FOR VOLTAGE CONTRAST ANALYSIS OF A WAFER USING A TILTED PRE-CHARGING BEAM

FIELD OF THE INVENTION

This invention relates to an apparatus and method for inspecting and testing semiconductors wafers during circuit fabrication and, in particular, for testing wafers in a voltage-contrast mode, especially using a tilted pre-charging beam of charged particles.

BACKGROUND OF THE INVENTION

Integrated circuits are very complex devices that include multiple layers. Each layer may include conductive material, isolating material and/or semi-conductive materials. These various materials are arranged in patterns, usually in accordance with the expected functionality of the integrated circuit. The patterns also reflect the manufacturing process of the integrated circuits.

Contact hole production is a common step in semiconductor device manufacturing. The contact holes are typically used to make electrical connections to a semiconductor or metal layer through an overlying non-conducting (dielectric) layer, such as an oxide layer. In order to produce contact holes, a layer of photoresist is first deposited on the wafer surface. The photoresist is exposed to patterned visible or ultraviolet radiation, hardened, and developed in order to form a "mask" over the wafer, with mask patterns corresponding to contact hole locations. Then the wafer is transferred to an etch station where contact holes are formed through the dielectric layer, down to the underlying semiconductor or metallic layer. The photoresist mask is then removed, and the contact holes are filled with metal. A similar masking and etching process is used in producing trenches or vias in the wafer surface.

In order to ensure consistent device performance, various characteristics of the contact openings must be carefully controlled at various locations across the wafer surface. (In the context of the present patent application and in the claims, the term "contact openings" refers to all structures of the type described above, including contact holes, vias, and trenches.)

In some cases the contact hole does not define a proper contiguous space that ends at the underlying semiconductor or metallic layer. In other words, the contact hole can be at least partially filled by non-conductive material that can alter the resistance of the conductor that is later formed within the contact hole. The non-conductive material can also form a barrier between the conductive material filled within the defective contact hole and the underlying layer. Such a defect can cause an electronic circuit to be electrically "open" instead of being electrically "closed". It can also result in higher impedance than expected from a contact that passes through a non-defective contact hole.

Voltage contrast techniques facilitate a determination of electrical properties of wafers and are based upon a detection of different charging conditions of different elements of an inspected sample. U.S. Pat. No. 6,627,884 of McCord, et al. titled "Simultaneous flooding and inspection for charge control in an electron beam inspection machine", and U.S. Pat. No. 6,586,736 of McCord titled "Scanning electron beam microscope having an electrode for controlling charge build up during scanning of a sample", which are incorporated herein by reference describe voltage contrast techniques.

Voltage contrast methods usually include a pre-charge stage that is followed by a scan and image stage. Some prior art methods use flooding guns that pre-charge a sample by scanning the sample with a normal incident charged particle beam. These techniques are suited to handle samples that include grounded underlying layers where underlying conducting layers remain discharged after the pre-charge stage while the oxide layer is charged, thus increasing the voltage contrast between open contact holes and their surrounding oxide layer.

FIG. 1 illustrates a cross section of a typical prior art SOI wafer 200. The lowest layer is a substrate 210. The substrate is usually made of silicone. An oxide layer (also referred to as BOX) 220 is manufactured above the substrate 210. The upper layer of the SOI wafer includes an inter-dielectric layer 240 through which contact holes 245 are fabricated. Trench insulators, such as oxide-made trench insulators 260 as well as silicone epilayer islands 230, 232, and 234, that are insulated from each other by trench isolators 260 are formed between the inter-dielectric layer 240 and the oxide layer 220.

Various wafers such as silicon over insulator (SOI) wafers and short loop wafers have sub surface structures that are intentionally floating. Thus, the pre-charging stage can charge both the inter-dielectric layer 240, any residual material within contact holes 245, and BOX layer 220. Thus, the efficiency of voltage techniques is greatly reduced.

There is a need to provide a system and method for an effective voltage contrast analysis.

SUMMARY OF THE INVENTION

A method for electrically testing a semiconductor wafer, the method including: receiving a wafer having a first layer that is at least partly conductive and a second layer formed over the first layer, following production of openings in the second layer; directing towards the wafer a first set of beams of charged particles that are oriented at a first set of angles in relation to the wafer, wherein each angle of the first set of angles deviates substantially from normal, so as to pre-charge an area of the second layer without substantially pre-charging the first layer; scanning the area of the wafer by a second set of beams of charged particle beam that are oriented at a second set of angles in relation to the wafer, and collecting charged particles scattered from the area wafer.

A system for electrically testing a semiconductor wafer, the system including: at least one charged particle beam source; at least one detector, adapted to collect charged particles scattered from the wafer; whereas the wafer comprises a first layer that is at least partly conductive and a second layer formed over the first layer, following production of openings in the second layer; whereas the system is adapted to: (i) direct towards the wafer a first set of beams of charged particles that are oriented at a first set of angles in relation to the wafer, whereas each angle of the first set of angles deviates substantially from normal, so as to pre-charge an area of the second layer without substantially pre-charging the first layer; (ii) scan the area of the wafer by a second set of beams of charged particles that are oriented at a second set of angles in relation to the wafer, and collect charged particles scattered from the area wafer.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 4 is a flow chart of a method 300 for performing voltage contrast analysis, according to an embodiment of the invention.

Figure 1:
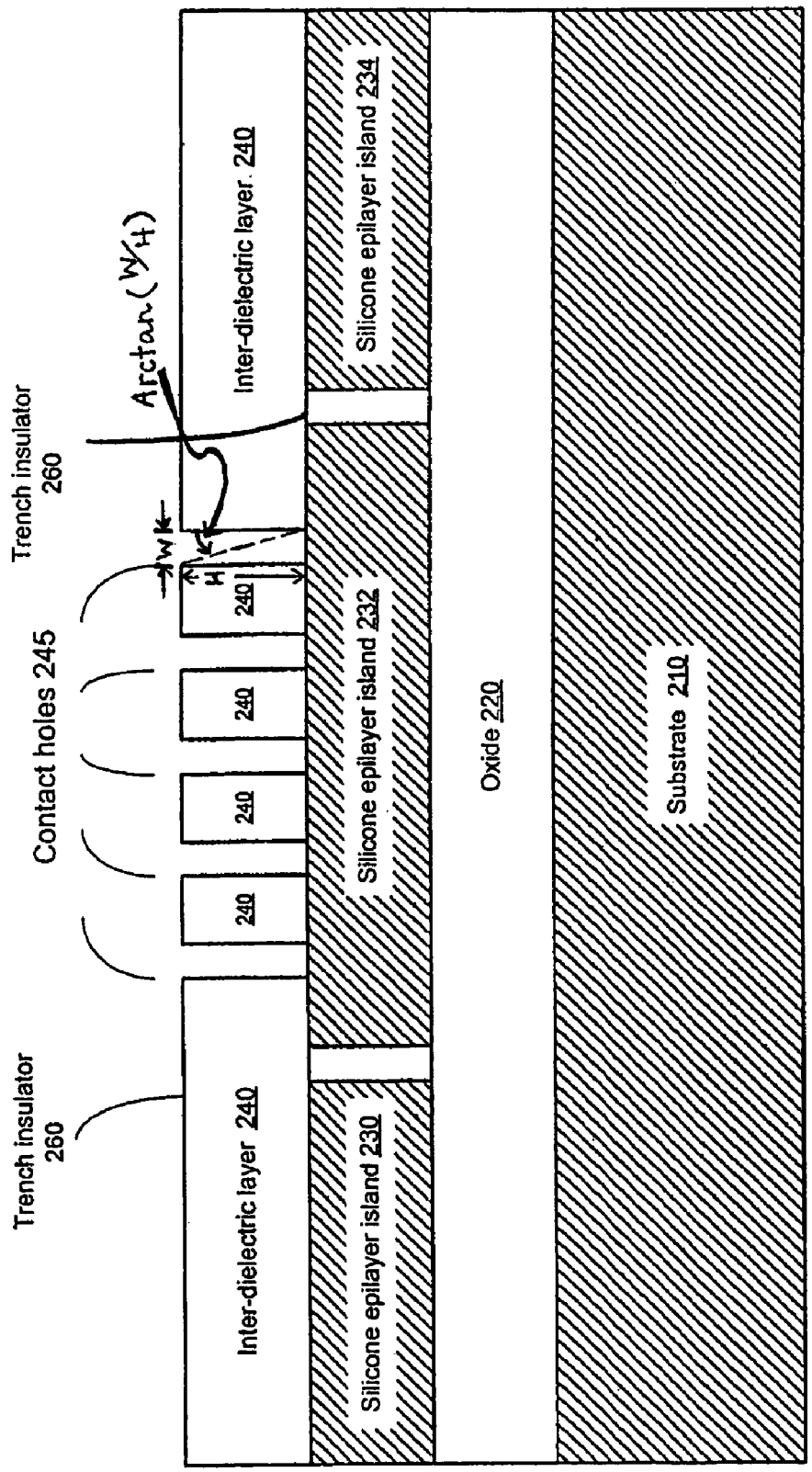
FIG. 1 illustrates a cross section of a typical prior art SOI wafer.

The following description relates to charged particle microscopes, such as Scanning Electron Microscopes (SEMs), such as step and repeat type SEMs, in which a wafer is scanned by repetitive steps of scanning an area of the wafer (said area defined by the field of view of the SEM) and mechanically introducing a movement between the wafer and SEM to facilitate the scanning of another area. Said movement may also be implemented by electrostatic and/or magnetic fields introduced by various electrostatic and/or magnetic elements such as lens, deflectors and the like. It is noted that other charged particles and even photons may be utilized for detecting voltage contrast. It is further noted that this invention may also be implemented by introducing a substantially constant movement between the SEM and the wafer. The movement may be linear or even rotational, and/or any combination of both movements.

Generally, a tilt mechanism can be implemented by mechanically tilting either the sample carrier relative to the charged particle beam column or the column relative to the sample's stage. A beam can be tilted by using single- or double-deflection. The use of a double-deflection technique, namely, pre-lens and in-lens deflection stages is known in the art.

The following descriptions refer, for convenience of explanation alone, to a system and method that use a single primary charged particle beam.

According to an embodiment of the invention, multiple charged particle beams can be used during the pre-charge stage. Alternatively or additionally, multiple primary charged particle beams can be utilized during the imaging stage. Systems and methods for producing multiple charged particle beams, either from multiple sources, or from a single source, are known in the art.

The term "set" as used in this application may include a single member. For example, the phrase "a first set of beams of charged particles that are oriented at a first set of angles" also includes a first beam that is oriented at a first angle", the "a second set of beams of charged particle beam that are oriented at a second set of angles" also includes a second beam that is oriented at a second angle.

It is noted that the multiple pre-charge beams can be directed towards the wafer at different directions, as long as they are tilted enough in relation to the wafer.

Using multiple pre-charge beams can increase the pre-charging uniformity for wafers with a topographical structure, such as, but not limited to, dual damascene. For dual damascene, the via/contacts are recessed into trenches which can run in both X and Y directions.

According to another embodiment of the invention, the pre-charge beam is not tilted and an angle of incidence in relation to the wafer is achieved by very strong over focusing of the pre-charge beam. The strong over-focusing provides a mixture of normal incidence and high angle electrons, but would be easier to design and implement than a tilted gun. It would also give a 360 degree population of high angle electrons for more uniform charging.

Figure 2:
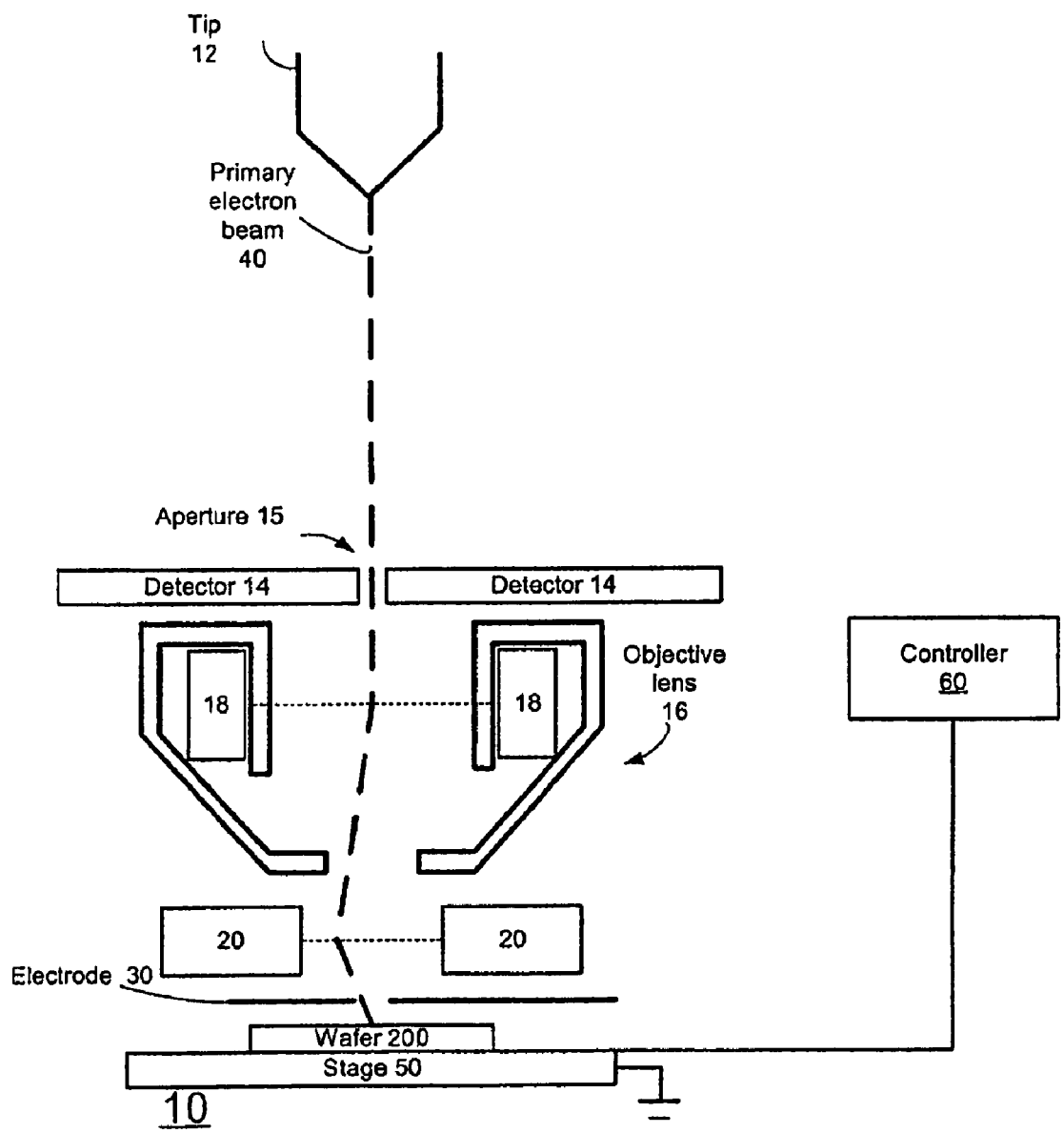
FIG. 2 illustrates a scanning electron microscope (SEM) that is capable of voltage contrast analysis, according to an embodiment of the invention.

FIG. 2 illustrates a double deflection tilt mechanism in which the primary charged particle beam is tilted by deflectors positioned in a plane of an objective lens and additional deflectors are located between the funnel of the objective lens and the inspected object. According to other embodiments of the invention, the amount of deflectors as well as their position can vary.

It is further noted that some SEM systems, such as the Applied Materials NanoSEM3D Applied Materials G2 SEM-Vision, provide this sort of beam tilt capability.

Various configurations of charged particle devices including SEMs, including an apparatus that allows tilting a charged particle beam is described in the following U.S. patents and U.S. patent applications of Petrov et al., all incorporated herein by reference: U.S. patent application 20040173746 titled "Method and system for use in the monitoring of samples with a charged particles beam", U.S. patent application 20030218133 titled "charged particle beam column and method for directing a charged particle beam"; U.S. patent application 20040056207 titled "deflection method and system for use in a charged particle beam column", and U.S. Pat. No. 6,674,075 titled "Charged beam apparatus and method for inspecting samples".

The invention can be applied to an SEM that includes at least one electrode that is positioned near the wafer, but this is not necessarily so. In such a case, the electrode has at least one opening for allowing the pre-charging beam as well as the scanning and imaging beam to pass therethrough.

The tilt angle is selected such that the pre-charging beam does not substantially interact with the bottom of the contact hole, but rather interacts with the sidewall of the contact hole that is a part of the inter-dielectric layer 240.

For example, assuming that: (i) the wafer is positioned along the X-Y plane and that openings are formed along the Z-axis, (ii) the depth (along the Z-axis) of a contact hole is H, (iii) the width (diameter, at the X-Y plane) of a contact hole is W, then the tilt angle, or more specifically the Z-axis trajectory of said angle $\alpha$, has to fulfill the following geometrical relationship: $\alpha <$ arctangent (W/H). W/H is also known as the aspect ratio of the contact hole. Each angle of a first set of angles (which may include one or more angles) shall fulfill this criterion. FIG. 1 depicts width W, depth H and angle arctangent (W/H).

The amount of charged particles that reaches the bottom of the contact hole can be also reduced by supplying positive voltage at the vicinity of the wafer.

FIG. 2 illustrates scanning electron microscope SEM 10 that is capable of voltage contrast analysis, according to an embodiment of the invention. The charged particle beams are illustrated during a pre-charge stage.

SEM 10 includes multiple components for providing a primary electron beam 40. The primary electron beam 40 is generated by SEM 10 and directed towards a wafer such as wafer 200. The primary electron beam 40 is used as a pre-charging beam during a pre-charge stage and can be used to irradiate wafer 200 during a scan and image stage. The characteristics (including intensity, tilt angle, landing energy and the like) of the primary electron beam 40 can be different from stage to stage, according to the use of said primary electron beam.

SEM 10 usually includes a large number of components, such as, but not limited to, an electron gun, one or more electrodes and anodes, one or more high voltage power supply and the like. For simplicity of explanation only tip 12 is shown.

The primary electron beam passes through an aperture (also referred to as opening) 15 formed within detector 14 and propagated towards a complex that includes an objective lens 16 and beam shift deflectors 18. The objective lens 16 usually includes multiple magnetic and electro-static components such as pole-pieces, caps, coils and the like, all being known in the art, but not illustrated in FIG. 2.

The path of the primary electron beam is altered twice. The beam shift deflectors 18 introduce a first shift while a second shift is introduced by tilt deflectors 20 that are positioned between the objective lens 16 and the inspected object. Two dashed horizontal lines illustrate the center of each pair of deflectors and the location of the shift. Deflectors 20 and 18 deflect the primary electron beam such that it is directed towards the object in a tilted manner. Thus, a tilted pre-charge beam is obtained.

It is noted that during an inspection phase, the primary electron beam can be normal to the inspected object or oriented with respect to an imaginary line that is normal to the inspected object.

During a scan and image stage, the primary electron beam interacts with wafer 200 and as a result, various types of electrons, such as secondary electrons, back-scattered electrons, Auger electrons and X-ray quanta are reflected or scattered. Secondary electrons can be collected easily and most SEMs mainly detect these secondary electrons. At least some of the scattered electrons subjected to the magnetic and/or electrostatic fields introduced by objective lens 16, and deflectors 18 and 20 are directed towards detector 14.

SEM 10 detects secondary electrons by detector 14. The detector 14 is connected to controller 60 that is capable of generating an image of the scanned wafer in response to the amplitude of collected secondary electrons and the location of the primary electron beam in relation to the wafer.

There are various detector configurations that can be applied. FIG. 2 illustrates a single in-lens detector but SEM 10 may include multiple detectors, at least one out-of-lens detector and the like. Typically, the detector includes a detecting segment that includes an opening, but other configurations can be implemented. For example, the opening can be formed between more than a single detecting segment.

SEM 10 may include an additional electrode 30 located near the inspected object, for improving the control of electromagnetic fields at the vicinity of the inspected object. Although FIG. 2 illustrates a single electrode, this is not necessarily so and multiple electrodes, as well as an electrode that is segmented into multiple portions, can be applied to control the charging of wafer 200.

Controller 60 is also connected to the stage 50 for controlling a mechanical movement introduced between wafer 200 and other parts of the SEM 10.

Controller 60 is capable of controlling other aspects of the SEM 10 operation, such beam deflection, beam focusing, beam generation, and the like. It is noted that the controller 60 can include multiple software and hardware components, and can be a single device or multiple devices.

Conveniently, during a scan and image stage, the stage 50 moves the wafer along a Y-axis while the electrical beam is deflected along an X-axis. This is not necessarily so and other combinations can be applied, including introducing mechanical movement along a first axis and deflecting the electron beam along a second axis that is not normal to the first axis. Furthermore, the direction of successive scans can be the same or opposite of each other.

Figure 3:
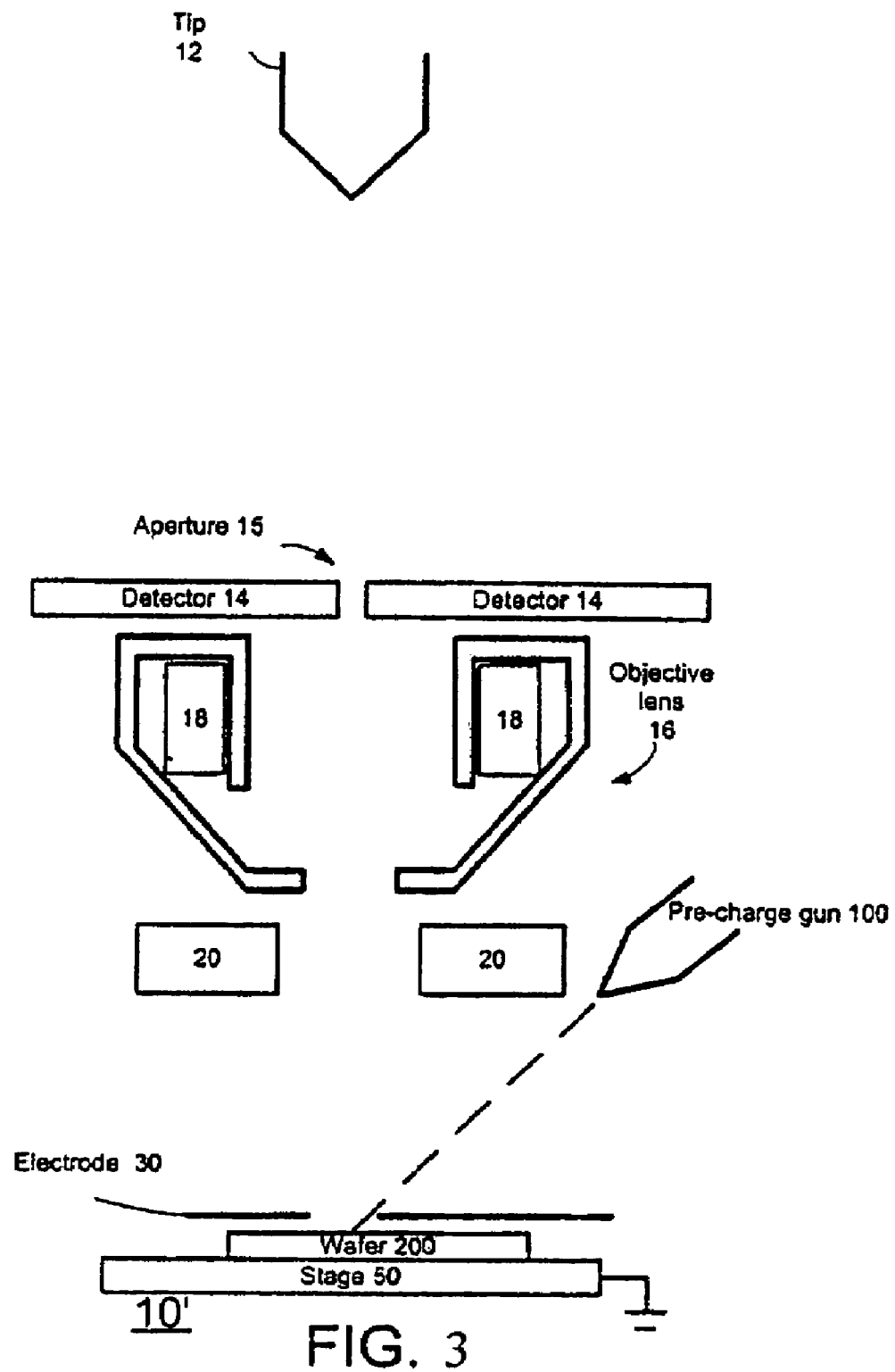
FIG. 3 illustrates an SEM that includes a pre-charge gun that provides a tilted pre-charge beam, according to an embodiment of the invention.

FIG. 3 illustrates a SEM 10' that includes a pre-charge gun 100 that provides a tilted pre-charge beam. If both the flooding beam and primary electron beam are applied simultaneously to substantially the same area, the working distance between the objective lens 16 and the wafer 200 may be bigger than the corresponding working distance of SEM 10.

Smaller working distances can be achieved if both beams can be directed to locations spaced apart from each other or directed to the same area at different time periods.

SEM 10' is illustrated as having tilting capabilities (for tilting a primary electron beam), but this is not necessarily so, especially if the tilt is applied to the pre-charge beam alone.

Pre-charge gun 100 is oriented so as to direct an oriented pre-charge beam towards the pre-charged object. Gun 100 can provide a relatively wide beam and can also be a flooding gun.

FIG. 4 is a flow chart of a method 300 for performing voltage contrast analysis, according to an embodiment of the invention.

Method 300 starts by stage 310 of receiving a wafer having a first layer that is at least partly conductive and a second layer formed over the first layer, following production of openings in the second layer.

Stage 310 is followed by stage 320 of directing towards the wafer a first set of beams of charged particles (also referred to as a pre-charge beam) that are oriented at a first set of angles in relation to the wafer, wherein each of the first set of angles deviates substantially from normal, so as to pre-charge an area of the second layer without substantially pre-charging the first layer. It is further noted that more than a single pre-charge beam can be oriented at the same angle.

Stage 320 is followed by stage 330 of scanning the area of the wafer by one or more second beam of charged particle beams that are oriented at one or more second angles in relation to the wafer, and collecting charged particles scattered from the area of the wafer. It is further noted that more than a single beam can be oriented at the same angle.

Conveniently, stage 330 includes introducing a mechanical movement between the wafer and the first beam of charged particles. Conveniently, the second angle is substantially ninety degrees.

Stage 330 is followed by stage 340 of generating an image of the area of the wafer in response to the collected charged particles.

According to an embodiment of the invention, the intensity of the first beam of charged particles differs from the intensity of the second beam of charged particles.

According to an embodiment of the invention, the first beam of charged particles is generated by a flooding gun. According to another embodiment of the invention, the first and second beams of charged particles are generated by the same source, such as the electron gun of an SEM. According to yet another embodiment of the invention, a combination of both the flooding gun and the electron gun of an SEM can be used.

Conveniently, stage 330 is preceded by a stage of introducing a mechanical tilt between the wafer and a charged particle beam source.

Conveniently, stage 310 is preceded by stage 305 of determining the first angle in response to an aspect ratio of at least one contact hole. This can be the contact hole having the smallest aspect ratio, but this is not necessarily so.

Conveniently, the first layer includes electrically floating chargeable elements.

According to another embodiment of the invention, the current of the primary electron beam can be altered so that during a scan and image stage, a primary electron beam characterized by a first current is used to scan the wafer, while during the discharge period, the wafer is scanned with a primary electron beam characterized by another current. Higher discharge currents can reduce the length of the discharge period.

While this invention has been described in connection with what is presently considered to be the most practical and preferred embodiment, it is to be understood that the invention is not limited to the disclosed embodiment. Rather, it is intended to cover various modifications within the spirit and scope of the appended claims.

The invention claimed is:

1. A method comprising:
    following production of openings in a second layer that is formed over a first, at least partially conductive, layer disposed on a wafer, directing towards the wafer a first set of beams of charged particles such that the first set of beams impinge onto the wafer oriented at a first set of angles in relation to the wafer, wherein each angle of the first set of angles deviates substantially from normal but is less than arctan(W/H) where W is a width of the openings and H is a depth of the openings, said impinging pre-charging an area of the second layer without substantially pre-charging the first layer; and
    scanning the area with a second, subsequent set of beams of charged particles that are oriented at a second set of angles in relation to the wafer, and collecting charged particles scattered from the area.

2. The method of claim 1 further comprising generating an image of the area after collecting the charged particles.

3. The method of claim 1 wherein scanning comprises introducing a mechanical movement between the wafer and the second set of beams of charged particles.

4. The method of claim 1 wherein an angle that belongs to the second set of angles is substantially ninety degrees.

5. The method of claim 1 wherein an intensity of a first beam of charged particles differs from an intensity of a second beam of charged particles.

6. The method of claim 1 wherein directing comprises generating a first beam of charged particles by a flooding gun.

7. The method of claim 1 wherein scanning is preceded by introducing a mechanical tilt between the wafer and a charged particle beam source.

8. The method of claim 1 comprising generating a first and a second charged particle beam by a certain beam source.

9. The method of claim 1 further comprising determining the first set of angles in response to an aspect ratio of at least one contact hole.

10. The method of claim 1 wherein the first layer comprises electrically floating chargeable elements.

11. A system for electrically testing a semiconductor wafer including a first, at least partly conductive, layer and a second layer formed over the first layer, there being openings in the second layer, the system comprising:
    at least one charged particle beam source generating
        (i) at least a first set of beams of charged particles directed toward the wafer such that the first set of beams impinge onto the wafer at a first set of angles in relation to the wafer, wherein each angle of the first set of angles deviates substantially from normal but is less than arctan(W/H) where W is a width of the openings and H is a depth of the openings, so as to pre-charge an area of the second layer without substantially pre-charging the first layer; and (ii) a second, subsequent set of beams of charged particles which scans the area at a second set of angles in relation to the wafer; and
    at least one detector collecting charged particles scattered from the area.

12. The system of claim 11 further comprising an image processor, coupled to the at least one detector, to generate an image of the area from the collected charged particles.

13. The system of claim 11 further comprising a stage for introducing a mechanical movement between the wafer and the first beam of charged particles.

14. The system of claim 11 wherein an angle of the second set of angles is substantially ninety degrees.

15. The system of claim 11 wherein an intensity of a first beam of charged particles differs from an intensity of a second beam of charged particles.

16. The system of claim 11 wherein the at least one particle beam source comprises a flooding gun to generate a first beam of charged particles.

17. The system of claim 11 wherein the system is arranged to introduce a mechanical tilt between the wafer and a charged particle beam source.

18. The system of claim 11 wherein the at least one charged particle beam source comprises a single charged particle beam source generating the first and second sets of beams.

19. The system of claim 11 wherein the system is arranged to determine the first set of angles in response to an aspect ratio of at least one contact hole.

20. The system of claim 11 wherein the first layer comprises electrically floating chargeable elements.

21. The system of claim 11 further comprising an electrode located at a vicinity of the wafer.

* * * * *